United States Patent

Etzrodt et al.

[11] Patent Number: 5,874,635
[45] Date of Patent: Feb. 23, 1999

[54] PREPARATION OF γ, δ-UNSATURATED KETONES BY THE CARROLL REACTION IN CYCLIC CARBONATES OR γ-LACTONES

[75] Inventors: Heinz Etzrodt, Neustadt; Manfred Stroezel, Ilvesheim; Dietmar Weller; Hagen Jaedicke, both of Ludwigshafen, all of Germany

[73] Assignee: BASF Aktiengesellschaft, Ludwigshafen, Germany

[21] Appl. No.: 965,024

[22] Filed: Nov. 5, 1997

[30] Foreign Application Priority Data

Nov. 14, 1996 [DE] Germany .......................... 19647117.6

[51] Int. Cl.[6] .................................................. C07C 45/51
[52] U.S. Cl. .......................... 568/383; 568/388; 568/398
[58] Field of Search .................................... 568/383, 388, 568/398

[56] References Cited

U.S. PATENT DOCUMENTS

| 2,638,484 | 5/1953 | Kimel . |
| 2,795,617 | 6/1957 | Kimel et al. . |

FOREIGN PATENT DOCUMENTS

| 1 068 696 | 5/1960 | Germany . |
| 2842149 | 4/1980 | Germany . |
| 695313 | 8/1953 | United Kingdom . |
| 886353 | 1/1962 | United Kingdom . |

OTHER PUBLICATIONS

M. F. Carroll. "Addition of αβ–Unsaturated Alcohols to the Active Methylene Group", Part I. The Action of Ethyl Acetoacetate on Linalool and Geraniol. J. Chem. Soc., 1940, pp. 704–706.

M. F. Carroll. "Addition of αβ–Unsaturated Alcohols to the Active Methylene Group", Part II. The Action of Ethyl Acetoacetate on Cinnamyl Alcohol and Phenylvinyl-carbinol. J. Chem. Soc., 1940, pp. 1266–1268.

J. Stewart Witzeman, et al. "Transacetoacetylation with tert–Butyl Acetoacetate: Synthetic Applications", J. Org. Chem., vol. 56, No. 5, (1991) pp. 1713–1718.

Primary Examiner—Gary Geist
Assistant Examiner—Sreeni Padmanabhan
Attorney, Agent, or Firm—Oblon, Spivak, McClelland, Maier & Neustadt, P.C.

[57] ABSTRACT

A process for preparing γ,δ-unsaturated ketones by
a) reacting vinylcarbinols or propargyl alcohols with alkyl acetoacetates or diketene and
b) thermally rearranging the resulting acetoacetates in the presence or absence of an aluminum catalyst to γ,δ-unsaturated ketones (Carroll reaction), wherein step a) and/or step b) is carried out in a cyclic carbonate of the formula I or a γ-lactone of the formula II

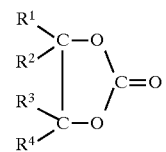

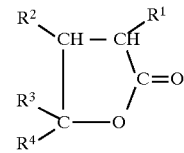

where $R^1$, $R^2$ and $R^3$ are H, or lower alkyl and $R^4$ is H, lower alkyl, phenyl or methoxymethyl, as solvent.

9 Claims, No Drawings

PREPARATION OF γ, δ-UNSATURATED KETONES BY THE CARROLL REACTION IN CYCLIC CARBONATES OR γ-LACTONES

The invention relates to the preparation of γ,δ-unsaturated ketones by the Carroll reaction in particularly advantageous solvents.

γ,δ-unsaturated ketones, such as 2-methyl-2-hepten-6-one, are intermediates which are in demand for preparing fragrances, vitamin A, vitamin E and pharmaceuticals. Hence there has never been a lack of attempts to prepare these compounds in advantageous manner.

One important known preparation method is the reaction of vinylcarbinols or propargyl alcohols with alkyl acetoacetates or diketene and subsequent thermal rearrangement of the resulting acetoacetates (Carroll reaction; cf. M. F. Carroll in J. Chem. Soc. (1940) 704–706 and 1266–1268).

U.S. Pat. No. 2,638,484 discloses the reaction of 2-methyl-3-buten-2-ol with diketene in the presence of metallic sodium, and the rearrangement of the resulting vinyldimethylcarbinol acetoacetate by cautious heating under reflux to the required 2-methyl-2-hepten-6-one. The disadvantages of this process are that the first step must be carried out at about 0° C., that continuous operation is impossible and that there are difficulties using sodium and diketene on the industrial scale.

U.S. Pat. No. 2,795,617 discloses carrying out the second step, ie. the rearrangement of the acetoacetates in the presence of catalytic amounts of aluminum trialkoxides, such as aluminum triisopropoxide, at from 135° to 165° C. The reaction is carried out in the absence of a solvent. The yields of γ,δ-unsaturated ketones in this process are still unsatisfactory.

In the process of GB 695 313 the acetoacetate of 2-methyl-3-buten-2-ol was heated at from 300° to 600° C. in the gas phase. However, the yields of unsaturated ketones range from only 13.8 to a maximum of 53.4 % based on acetoacetate.

In the process of GB 886 353, the rearrangement of the allyl acetoacetates takes place by heating them in the presence of aluminum tri(acetylacetonates) at from 140° to 170° C. The yields in this process are also unsatisfactory.

In order to avoid the problematic use of diketene for preparing the allyl acetoacetates, in reactions on the industrial scale diketene is often replaced by the lower alkyl esters of acetoacetic acid which are easily prepared therefrom. At temperatures above 100° C., the alcohol is eliminated from the acetoacetic ester and can be distilled off (cf. J. Org. Chem. 56 (1991), 1713–1718).

When 2-methyl-3-buten-2-ol (boiling point 98° C.) is reacted by this method, the temperature of from 120° to 220° C. which is required for the subsequent rearrangement of the allyl acetoacetate is reached under atmospheric pressure only by employing a large excess ethyl acetoacetate (boiling point 169° C.) (cf. DBP 1 068 696), but, under the reaction conditions, the acetoacetic ester also reacts with itself, and the dehydroacetic acid which is formed, among other byproducts, also initiates other side reactions.

It is an object of the present invention to improve the process for preparing γ,δ-unsaturated ketones by reacting vinylcarbinols or propargyl alcohols with alkyl acetoacetates or diketene and subsequently thermally rearranging the resulting acetoacetates in such a way that no large excess of acetoacetic esters is required, and that the rearrangement of the acetoacetates can be carried out continuously and with very good yields under atmospheric pressure.

We have found that this object is achieved by the considerable increase in the rate of Carroll reactions in 5-membered cyclic lactones and 5-membered cyclic carbonates. The temperatures of more than 150° C. which are required for the rearrangement are achieved under atmospheric pressure in the relatively high-boiling 5-membered cyclic lactones and 5-membered cyclic carbonates, because low-boiling methylbutenol (boiling point 98° C.) rapidly reacts with the acetoacetic ester and forms 2-methyl-2-hepten-6-one. The methanol formed from methyl acetoacetate distills out continuously at the reaction temperatures of from 120° to 220° C. without degrading the cyclic ladtone or cyclic carbonate used as solvent.

The invention accordingly relates to a process for preparing γ,δ-unsaturated ketones by a) reacting vinylcarbinols or propargyl alcohols with alkyl acetoacetates or diketene and b) thermally rearranging the resulting acetoacetates in the presence or absence of an aluminum catalyst to γ,δ-unsaturated ketones (Carroll reaction), wherein step a) and/or step b) is carried out in a cyclic carbonate of the formula I or a γ-lactone of the formula II

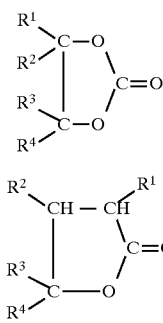

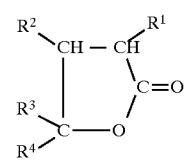

where $R^1$, $R^2$ and $R^3$ are H, methyl or ethyl, preferably H or methyl and $R^4$ is H, methyl, ethyl, isopropyl, phenyl or methoxymethyl, as solvent.

Suitable 5-membered cyclic carbonates of the formula I are, besides the usual alkylene carbonates such as ethylene carbonate, 1,2-propylene carbonate, isobutylene carbonate and 1,2-butylene carbonate, ie. carbonates of the formula I, where $R^1$ to $R^4$ are H or methyl, or $R^1$ to $R^3$ are H or methyl and $R^4$ is ethyl, also those where $R^1$ to $R^3$ can additionally be ethyl, and $R^4$ is H, methyl, ethyl, isopropyl, phenyl or methoxymethyl.

The cyclic carbonates used according to the invention can be prepared at extremely reasonable cost even on the industrial scale by reacting the corresponding alkylene oxides with $CO_2$. Their boiling points are generally so high that temperatures of 170° C. can be reached without difficulty under atmospheric pressure. They are non-toxic (the oral $LD_{50}$ for rats is, for example, 29,000 mg/kg for 1,2-propylene carbonate and 10,000 mg/kg for ethylene carbonate), which is essential for the preparation of vitamin precursors, and their biodegradability is good (cf. "Alkylencarbonate", brochure of Hüls AG, July 1991).

Particularly suitable 5-membered cyclic lactones of the formula II which may be mentioned are γ-butyrolactone, 3-methyl-γ-butyrolactone, 3,4-dimethyl-γ-butyrolactone, 4,5-dimethyl-γ-butyrolactone and 5-ethyl-γ-butyrolactone, especially γ-butyrolactone.

The γ-butyrolactones of the formula II used according to the invention can also be prepared on the industrial scale advantageously by dehydrogenation of the corresponding butanediols.

Surprisingly, the alkanol formed in the reaction attacks the cyclic carbonates or lactones so little under the reaction conditions that, for example when propylene carbonate is used, the solvent can be reused for up to 10 reaction cycles without 10 any purification (cf. Example 1). The cyclic carbonate or lactone removed after the isolation of the γ,δ-unsaturated ketone can be fed into new reaction cycles without replenishing the catalyst. Moreover, residues of unreacted acetoacetate remain in the solvent and are not lost.

The 5-membered cyclic carbonates and 5-membered cyclic lactones are generally used in amounts of from 50 to 1000%, preferably 100 to 500%, of the weight of γ,δ-unsaturated ketone formed.

The vinylcarbinols or propargyl alcohols which can be employed in the process according to the invention are alcohols of the formula III

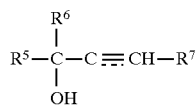

where
- $R^5$ is a branched or unbranched, saturated or olefinically mono- or polyunsaturated aliphatic or cycloaliphatic-aliphatic radical which has 1 to 20 carbon atoms and may be substituted by alkoxy groups or halogen,
- $R^6$ is H or a lower alkyl group, preferably methyl or ethyl,
- $R^7$ is H or a lower alkyl group, preferably H, and the dotted line may mean another bond.

Examples which may be mentioned are 2-methyl-3-buten-2-ol, nerolidol, 10,11-dihydronerolidol, linalool, 6,7-dihydrolinalool, geranyllinalool, isophytol, or 1-alkyn-3-ols, such as dehydrolinalool and 2-methyl-3-butyn-2-ol. The reaction according to the invention takes place particularly advantageously on use of 2-methyl-3-buten-2-ol, ie. a compound of the formula III, where $R^5$ and $R^6$ are methyl and $R^7$ is H.

The process according to the invention is generally carried out by reacting in the first step the allyl or propargyl alcohols as in the prior art, ie. without solvent or in a solvent known for the reaction, such as diethyl ether, toluene or xylene, in the absence or in the presence of a basic catalyst known for the reaction, with diketene, and carrying out the subsequent thermal rearrangement of the resulting acetoacetates, where appropriate after the solvent has been distilled off, and in the presence or absence of an aluminum catalyst, in a 5-membered cyclic carbonate of the formula I or a γ-lactone of the formula II as solvent, or else, advantageously, carrying out both the reaction of the vinylcarbinols or propargyl alcohols with alkyl acetoacetates or diketene and the subsequent thermal rearrangement of the resulting acetoacetates, in the presence or absence of an aluminum catalyst, in a 5-membered cyclic carbonate of the formula I or a γ-lactone of the formula II as solvent. The latter variant of the process according to the invention has the great advantage that virtually one-pot reaction is possible.

Thus, it is essential for the process of the present invention that, in every case, the initially formed acetoacetates are thermally rearranged in a 5-membered cyclic carbonate of the formula I or a γ-lactone of the formula II.

The reaction of allyl or propargyl alcohols with diketene is well-known to be carried out in the presence of basic catalyst. Those which may be mentioned are tertiary amines such as pyridine and, in particular, para-N,N-dimethylaminopyridine. If both the reaction of the vinylcarbinols or propargyl alcohols with diketene and the subsequent thermal rearrangement are carried out in 5-membered cyclic carbonates or 5-membered cyclic lactones, ie., virtually a one-pot reaction, it is advisable to carry out the first step in the absence of a basic catalyst or at least in the presence of only small amounts thereof.

The temperatures for the thermal rearrangement are generally from 120° to 220° C., preferably from 140° to 190° C.

The thermal rearrangement can be carried out in the absence or in the presence of one of the known aluminum catalysts.

Examples of suitable aluminum catalysts known for the reaction are aluminum alcoholates, such as aluminum tri (isopropoxide) or one of the aluminum tri(butoxides); or else aluminum tri(acetylacetonate) or aluminum tri(alkyl acetylacetates), such as aluminum tri(methyl acetylacetate).

It is particularly advantageous for the preparation of 2-methyl-2-hepten-6-one, which is important for preparing vitamin A and vitamin E, by reacting 2-methyl-3-buten-2-ol and methyl acetoacetate if both the reaction of the methylbutenol with methyl acetoacetate and the thermal rearrangement of the resulting acetoacetates are carried out in a 5-membered cyclic carbonate of the formula I or a 5-membered cyclic lactone of the formula II, ie. virtually in a one-pot reaction.

The procedure in this case is advantageously such that an aluminum catalyst known for this reaction is heated in a 5-membered cyclic carbonate of the formula I or 5-membered cyclic lactone of the formula II to about 170° to 180° C., and a mixture of the methylbutenol and the methyl acetoacetate are slowly metered into this hot mixture, during which the $CO_2$ which is formed escapes and lower boilers are distilled off. After the reaction is complete, the methylheptenone can then be distilled off under atmospheric or reduced pressure, and the distillation residue can be used anew as reaction medium.

Since no significant decrease in the yield was observed even after the reaction medium according to the invention had been reused 9 times, it can be assumed that the reaction can also be carried out continuously.

The process according to the invention makes it possible to prepare the γ,δ-unsaturated ketones which are in demand in particular as intermediates for preparing fragrances, vitamin A, vitamin E and drugs in a simple manner and in very good yields also on the industrial scale.

EXAMPLE 1

Reaction of 2-methyl-3-buten-2-ol with methyl acetoacetate in 1,2-propylene carbonate a) A mixture of 29.03 g (0.25 mol) of methyl acetoacetate (MAA; purity 98%) and 23.68 g (0.275 mol) of 2-methyl-3-buten-2-ol (MBE; purity 94%) was pumped into a mixture of 45 g of 1,2-propylene carbonate and 2.8 g of a separately prepared (as disclosed in GB 886 353) aluminum tri(methyl acetylacetate) catalyst over the course of 2 hours (h) while stirring at 180° C. During this time, $CO_2$ was evolved, and 8 g of low boilers which consisted of about ⅔ methanol and about ⅓ unreacted 2-methyl-3-buten-2-ol distilled out. The reaction mixture was subsequently stirred at 180° C. for 30 minutes (min) and then cooled, and the required 2-methyl-2-hepten-6-one was distilled out under 100 mbar.

b) The distillation residue resulting from this was again mixed with the abovementioned amounts of MAA and MBE over the course of 2 h at 180° C., the mixture was stirred at 180° C. for 30 min and then cooled, and the resulting 2-methyl-2-hepten-6-one was distilled out.

c) Step b) was repeated 8 times more. The average yield of 2-methyl-2-hepten-6-one for all 10 batches was 88% of theory based on reacted MBE (determination by gas chromatography with internal standard).

EXAMPLE 2 a) Preparation of 10,11-dihydronerolidol acetoacetate from 10,11-dihydronerolidol and diketene 5.05 g (0.074 mol) pf diketene were added dropwise over the course of 20 min to a solution of 9 g (0.04 mol) of 10,11-dihydronerolidol and 60 mg of para-N,N-dimethylaminopyridine in 50 ml diethyl ether at 20° C. The solvent was then distilled out at 40° C.

b) Carroll-reaction of 10,11-dihydronerolidol acetoacetate in 1,2-propylene carbonate The reaction mixture obtained in stage a) was, without further purification, added dropwise over the course of 20 min to a mixture of 20 ml of 1,2-propylene carbonate and 300 mg of aluminum tri(methyl acetylacetate) at 180° C. The mixture was subsequently stirred at 180° C. for 10 min and then extracted 2× with 50 ml of heptane each time. The combined extracts were distilled. The yield of 13,14-dihydrofarnesylacetone was 88% of theory based on 10,11-dihydronerolidol.

Once again, the propylene carbonate containing the catalyst can be reused.

EXAMPLE 3 a) Reaction of 2-methyl-3-buten-2-ol with methyl acetoacetate in γ-butyrolactone A solution of 100 ml of γ-butyrolactone and 5.6 g of the catalyst indicated in Example 1 was heated to from 170 to 180° C., and to this was added dropwise over the course of 30 min, while stirring at 170° to 180° C. a mixture of 58.06 g (0.5 mol) of MAA and 47.36 g (0.55 mol) of MBE. The mixture was subsequently stirred at 170° C. for 30 min and cooled, and the resulting 2-methyl-2-hepten-6-one was distilled off under atmospheric pressure. 59.7 g of an 86% pure methylheptenone were isolated in this way.

b) The distillation residue resulting in stage a) was again mixed over the course of 30 min at 170° to 180° C. with a mixture of 58.06 g of MAA and 47.36 g of MBE, the mixture was then stirred at 170° C. for 30 min and cooled, and the methylheptenone was distilled out.

c) Step b) was repeated 3 more times. The average yield of 2-methyl-2-hepten-6-one for all 5 batches was 85% of theory based on MBE.

EXAMPLE 4

Reaction of 2-methyl-3-butyn-2-ol with methyl acetoacetate in 1,2-propylene carbonate A mixture of 5.3 g of the aluminum tri(methyl acetylacetate) catalyst mentioned in Example 1 and 85 g of 1,2-propylene carbonate was heated to 170° C. and, at this temperature a mixture of 55 g (0.47 mol) of methyl acetoacetate and 43.7 g (0.52 mol) of 2-methyl-3-butyn-2-ol was metered in at a constant rate over the course of 4 h. After the addition was complete, the mixture was stirred at 170° C. for 30 min. During this time, $CO_2$ was evolved and low boilers distilled out. The reaction mixture was subsequently cooled, and the 2-methyl-2,4-heptadien-6-one which was formed was distilled out under about 100 mbar. This resulted in 42 g of pure 2-methyl-2,4-heptadien-6-one, which corresponds to a yield of 72% of theory based on reacted 2-methyl-3-butyn-2-ol.

We claim:

1. A process for preparing γ,δ-unsaturated ketones, which comprises:

a) reacting vinylcarbinols or propargyl alcohols with alkyl acetoacetates or diketene, and b) thermally rearranging the resulting acetoacetates in the presence or absence of an aluminum catalyst to γ,δ-unsaturated ketones, and wherein step a) or step b) or both is carried out in a cyclic carbonate of the formula (I) or a γ-lactone of the formula (II) as a solvent:

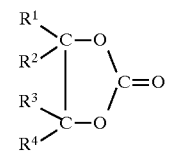

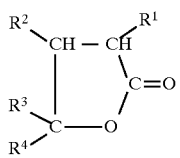

wherein $R^1$, $R^2$ and $R^3$ are H, methyl or ethyl; and $R^4$ is H, methyl, ethyl, isopropyl, phenyl or methoxymethyl.

2. The process of claim 1, wherein step a) or step b) or both is carried out in a solvent selected from the group consisting of ethylene carbonate, 1,2-propylene carbonate, 1,2-butylene carbonate and isobutylene carbonate.

3. The process of claim 1, wherein step a) or step b) or both is carried out in a solvent selected from the group consisting of γ-butyrolactone, 3-methyl-γ-butyrolactone, 3,4-dimethyl-γ-butyrolactone, 4,5-dimethyl-γ-butyrolactone or 5-ethyl-γ-butyrolactone.

4. The process of claim 1, wherein step b) is carried out at from about 120° C. to 220° C.

5. The process of claim 4, wherein step b) is carried out at from about 150° C. to 200° C.

6. The process of claim 1, wherein $R^1$, $R^2$ and $R^3$ are H or methyl.

7. The process of claim 1, which comprises preparing 2-methyl-2-heptene-6-one by slowly adding a mixture of 2-methyl-3-buten-2-ol and methyl acetoacetate at from 170° C. to 180° C. into a mixture of the cyclic carbonate of the formula (I) or the γ-lactone of the formula (II) and said aluminum catalyst, distilling off methyl heptenone after reaction is complete and using a distillation residue therefrom anew as a reaction medium.

8. The process of claim 1, wherein the cyclic carbonate of the formula (I) or the γ-lactone of the formula (II) is used in an amount of from 50 to 1000% of the weight of the γ,δ-unsaturated ketone formed.

9. The process of claim 8, wherein the cyclic carbonate or the γ-lactone is used in an amount of from 100 to 500% of the weight of the γ,δ-unsaturated ketone formed.

* * * * *